(12) United States Patent  
Zeelie et al.

(10) Patent No.: US 11,795,421 B2  
(45) Date of Patent: Oct. 24, 2023

(54) MICROALGAE PRODUCTION PROCESS AND EQUIPMENT

(71) Applicant: NELSON MANDELA UNIVERSITY, Port Elizabeth (ZA)

(72) Inventors: Bernard Zeelie, Port Elizabeth (ZA); Johan Pieter Barnard, Port Elizabeth (ZA)

(73) Assignee: Nelson Mandela University, Port Elizabeth (ZA)

( * ) Notice: Subject to any disclaimer, the term of this patent is extended or adjusted under 35 U.S.C. 154(b) by 463 days.

(21) Appl. No.: 15/740,062

(22) PCT Filed: Jul. 1, 2016

(86) PCT No.: PCT/IB2016/053966  
§ 371 (c)(1),  
(2) Date: Dec. 27, 2017

(87) PCT Pub. No.: WO2017/002084  
PCT Pub. Date: Jan. 5, 2017

(65) Prior Publication Data  
US 2018/0195032 A1  Jul. 12, 2018

(30) Foreign Application Priority Data  
Jul. 1, 2015 (GB) ..................... 1511545

(51) Int. Cl.  
*C12M 1/12* (2006.01)  
*A01G 33/00* (2006.01)  
*C12M 1/00* (2006.01)

(52) U.S. Cl.  
CPC ............. *C12M 21/02* (2013.01); *A01G 33/00* (2013.01); *C12M 23/06* (2013.01); *C12M 23/18* (2013.01); *C12M 27/18* (2013.01)

(58) Field of Classification Search  
USPC ........ 47/1.4; 435/257.1–257.6, 283.1–309.4, 435/295.2, 296.1, 289.1, 292.1  
See application file for complete search history.

(56) References Cited

U.S. PATENT DOCUMENTS 5,447,629 A * 9/1995 Chaumont ............. C12M 25/14  
    210/96.1  
8,198,076 B2 * 6/2012 Hu ......................... C12M 41/12  
    435/292.1

(Continued)

FOREIGN PATENT DOCUMENTS

CA    2764291 A1   7/2013  
CN   102448286 A   5/2012

(Continued)

OTHER PUBLICATIONS

International Search Report and Written Opinion corresponding to PCT/IB2016/053966 dated Oct. 5, 2016, 11 pages.

(Continued)

*Primary Examiner* — Andrea M Valenti  
(74) *Attorney, Agent, or Firm* — Mintz, Levin, Cohn, Ferris, Glovsky and Popeo, P.C.

(57) ABSTRACT

Microalgae cultivation equipment for the cultivation of microalgae is provided in which a raceway is modified so as to contain multiple generally upright photobioreactor columns spaced apart along its length so as to increase the total surface area of liquid growth medium directly exposed to light and to improve the transfer of $CO_2$ from the gas-phase to the liquid-phase by providing adequate height inside the vertical photobioreactor columns. The lowermost ends of the photobioreactor columns are immersed inside the liquid growth medium in the raceway component and are fed with liquid growth medium by a circulation promoting facility circulating the liquid growth medium from the raceway through the photobioreactor columns to become discharged (Continued)

back into the raceway. Gas inlets provide $CO_2$ containing gas bubbles passing upwards in each of the photobioreactor columns. One or more paddle wheels or jet pumps induce a flow of liquid growth medium within the raceway.

12 Claims, 6 Drawing Sheets

(56) References Cited

U.S. PATENT DOCUMENTS

| | | | |
|---|---|---|---|
| 9,932,549 B2* | 4/2018 | Gross | C12N 11/02 |
| 2008/0311646 A1* | 12/2008 | Cong | C12M 29/08 |
| | | | 435/257.1 |
| 2010/0267104 A1* | 10/2010 | Green | C12M 31/08 |
| | | | 435/173.1 |
| 2011/0020913 A1* | 1/2011 | Rispoli | C12M 29/02 |
| | | | 435/257.1 |
| 2011/0027875 A1* | 2/2011 | Cathcart | C12M 23/44 |
| | | | 435/292.1 |
| 2011/0104790 A1* | 5/2011 | Kassebaum | C12M 23/22 |
| | | | 435/257.1 |
| 2012/0252105 A1 | 10/2012 | Ahrens et al. | |
| 2013/0059369 A1 | 3/2013 | Lin et al. | |
| 2013/0230904 A1* | 9/2013 | Suryo | C12M 31/06 |
| | | | 435/257.1 |
| 2014/0315290 A1* | 10/2014 | Mottahedeh | C12M 31/00 |
| | | | 435/288.7 |

FOREIGN PATENT DOCUMENTS

| | | | | |
|---|---|---|---|---|
| CN | 202246641 | * | 5/2012 | C12M 21/02 |
| CN | 202246641 U | | 5/2012 | |
| CN | 103571736 A | | 2/2014 | |
| CN | 103627623 A | | 3/2014 | |
| CN | 103865758 A | | 6/2014 | |
| CN | 10461121 A | | 5/2015 | |
| EP | 2712917 A1 | | 4/2014 | |
| EP | 2840128 A1 | * | 2/2015 | C12M 1/00 |
| JP | 2000139444 A | | 5/2000 | |
| WO | 2009/077087 A1 | | 6/2009 | |
| WO | 2011/053893 A2 | | 5/2011 | |
| WO | 2011/106038 A1 | | 9/2011 | |

OTHER PUBLICATIONS

Extended European Search Report corresponding to EP 16817361.5 dated Feb. 5, 2019, 7 pages.
Database WPI Week 201568 Thomason Scientific, London, GB; AN 2015-56669B, XP002788271; Abstract (see, also, English translation CN104611221A).
Zhiyong Li et al., "Cell Engineering," Higher Education Press, p. 198 (Jun. 2008).
Xu Zhang et al., "Studies on the Application of Airlift allgal Photo-bioreactor," Ocean Science, vol. 24, No. 5, p. 14-17 (2000).

* cited by examiner

MICROALGAE PRODUCTION PROCESS AND EQUIPMENT

CROSS-REFERENCE(S) TO RELATED APPLICATIONS

This application claims priority from United Kingdom patent application number 1511545.4 filed on 1 Jul. 2015, which is incorporated by reference herein.

FIELD OF THE INVENTION

This invention relates to a process and equipment for the cultivation of microalgae that can be used for many different purposes.

BACKGROUND TO THE INVENTION

State-of-the-art microalgal cultivation systems generally fall into one of two major classifications, namely closed systems (photobioreactor technology) and open systems (open pond or raceway technology).

Photobioreactors are culturing systems in which light passes through transparent reactor walls that are made UV-resistant material to reach the microalgae cells being cultivated within the reactor.

Open ponds or raceways, on the other hand, are open systems in which sunlight impinges on the surface of a liquid culture medium that is typically circulated in an endless channel known as a raceway. Both types of cultivation systems have their advantages and drawbacks.

Open systems are simple and relatively inexpensive to build; they require minimal labour for their operation and maintenance; but are more susceptible to microbial and other sources of contamination than are closed system photobioreactors. Open ponds also suffer to a greater extent from water loss through evaporation. One of the main shortcomings of a traditional raceway is its poor surface area to volume ratio, which has a direct impact upon the system's ability to capture photons effectively. A second main shortcoming of open systems is that they have very poor $CO_2$ absorption capabilities due to their generally shallow nature (liquid growth medium height).

Photobioreactors on the other hand, have substantially lower risk of contamination; minimize water losses; and provide greater control of variables that affect microalgae growth such as improved surface area to volume ratios and $CO_2$ absorption. However, this comes at the expense of high capital, maintenance, and operating costs. Tubular photobioreactor designs normally need an air compressor or blower and a centrifugal pump for culture circulation and gas exchange. Energy efficiency in terms of biomass productivity per energy input is always of paramount importance.

Hybrid systems combine features of open ponds and photobioreactors. Two main types of hybrid systems have been reported. One is in the form of a covered open pond which reduces the possibility of contamination, evaporative losses, and $CO_2$ desorption and loss. The other type is a partially filled tubular design widened and inflated to approximate an open pond, this design being mainly aimed at reducing costs.

Hybrid systems of these general types have both been evaluated for commercial cultivation.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided microalgae cultivation equipment for the cultivation of microalgae, the cultivation equipment having a raceway component with a raceway defining an endless channel for the circulation of liquid growth medium therein by means of a flow inducing arrangement for inducing a flow of liquid growth medium within the endless channel of the raceway, the cultivation equipment being characterized in that it has an integrated second component comprising multiple upright photobioreactor columns spaced apart along the length of the raceway and that are supported in an upright condition such that their lowermost ends discharge in use liquid growth medium into liquid growth medium in the raceway, a circulation promoting facility for causing liquid growth medium to circulate from the raceway component through the photobioreactor columns to become discharged back into the raceway; and one or more gas inlets for providing gas bubbles, in use, passing upwards in each of the photobioreactor columns.

Further features of the invention provide for the equipment to be configured such that in use an exposed surface area of growth medium to direct light or sunlight in the photobioreactor columns is between 50 and 200% that of an exposed surface area of growth medium in the raceway alone without the photobioreactor columns and preferably from 50 to 120%; for the integrated photobioreactor columns to contain between 5 and 30% of the total volume of liquid growth medium in the modified raceway cultivation equipment; for the endless channel to be of generally oval shape in plan view; for the lower ends of the photobioreactor columns to be arranged to be immersed in liquid growth medium in the raceway, in use; for the flow inducing arrangement to be one or more horizontal paddle wheels rotatable by a power source such as an electric motor or, alternatively, for one or more water jets to be directed in the general direction in which flow is to be induced within the channel of the raceway, or both; for the circulation facility to be one or more low shear pumps for withdrawing liquid growth medium from the raceway component and transferring it either directly to uppermost regions of the photobioreactor columns or alternatively by way of a manifold pipe interconnecting the upper ends of the photobioreactor columns so as to distribute liquid growth medium to the upper ends of multiple photobioreactor columns; alternatively, for a low-shear pump to pump liquid growth medium into the photobioreactor columns from the bottom to cause it to flow upwards and overflow back into the raceway by way of a separate overflow tube conveniently concentric with the photobioreactor column; and for an elevated gas separation reservoir to be associated with the upper ends of the photobioreactor columns for discharging oxygen enriched gasses from the photobioreactor columns and to function as a de-misting zone so as to inhibit liquid loss from the vertical photobioreactor columns.

Yet further features of the invention provide for an inlet to be provided for $CO_2$ enriched air to be sparged into each individual photobioreactor column so as to enable control of the available $CO_2$ inside the entire body of growth medium by either increasing or decreasing the liquid flow rate through the photobioreactor columns, or by increasing or decreasing the concentration of $CO_2$ in the air, or both; for the raceway itself to have no inlets for gas directly to the raceway; for sufficient air to be admixed with $CO_2$ present in gasses introduced into the liquid growth medium to cause turbulence inside the photobioreactor columns; for a pH monitor to be provided to control the pH of the growth medium with narrow limits through adjusting the $CO_2$ content of the air used to sparge the vertical photobioreactor columns or by adjusting the rate of flow of growth medium through the vertical photobioreactor columns; and for the photobioreactor columns to have one or more outlet pipes arranged generally horizontally to return liquid growth medium to the raceway below the liquid surface of growth medium in the raceway and which may optionally be inclined in a direction different from the general direction of flow in the raceway and more particularly may be directed either upwards or downwards relative to the general direction of flow in the raceway or inclined at a sideways angle to the general direction of flow, or both, in order to create a desired mixing action of algae and liquid growth medium in the raceway.

It is to be understood that, as a general rule, whilst the lower ends of the photo bioreactor columns will generally extend into the liquid growth medium in the raceway, it is not essential that this arrangement be employed and the photo bioreactor columns could be arranged to be somewhat offset from the raceway whilst still delivering liquid growth medium back into the liquid growth medium in the raceway.

It should be noted that the term photobioreactor column as used in this specification means a tubular column within which movement of liquid growth medium can take place.

In order that the above and other features of the invention may be more fully understood one embodiment thereof and an expanded description of the invention follows with reference to the accompanying drawings.

DETAILED DESCRIPTION WITH REFERENCE TO THE DRAWINGS

Figure 1:
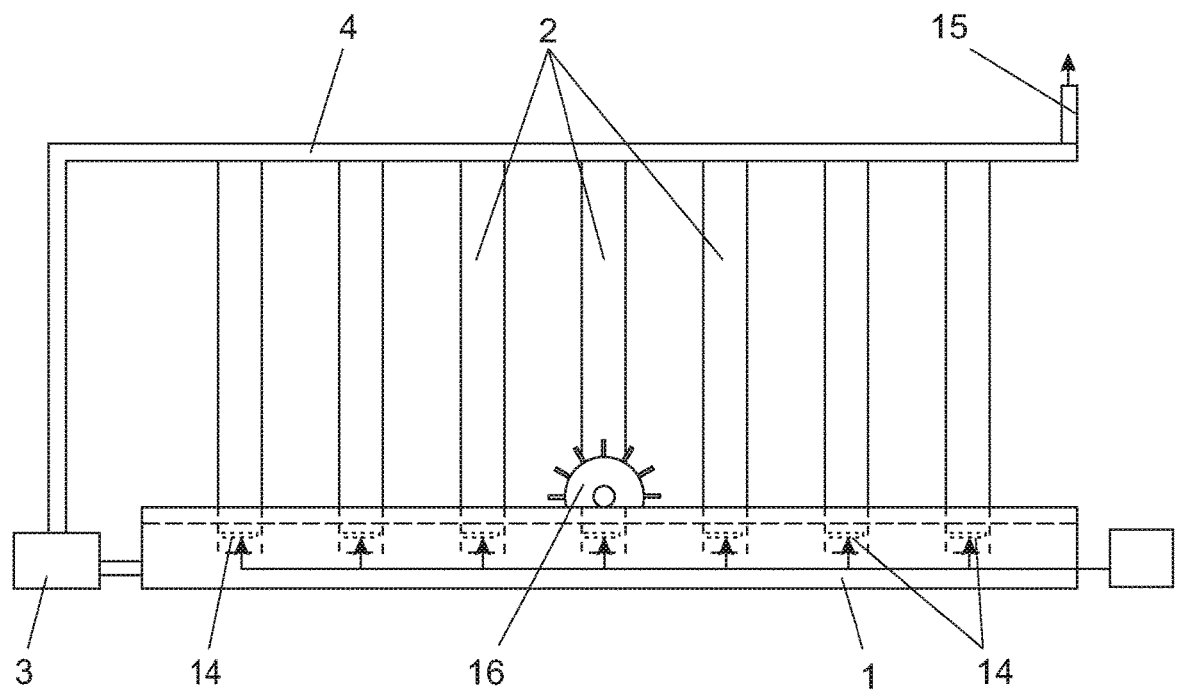
FIG. 1 is a schematic elevation of one embodiment of prototype according to the invention.
Figure 2:
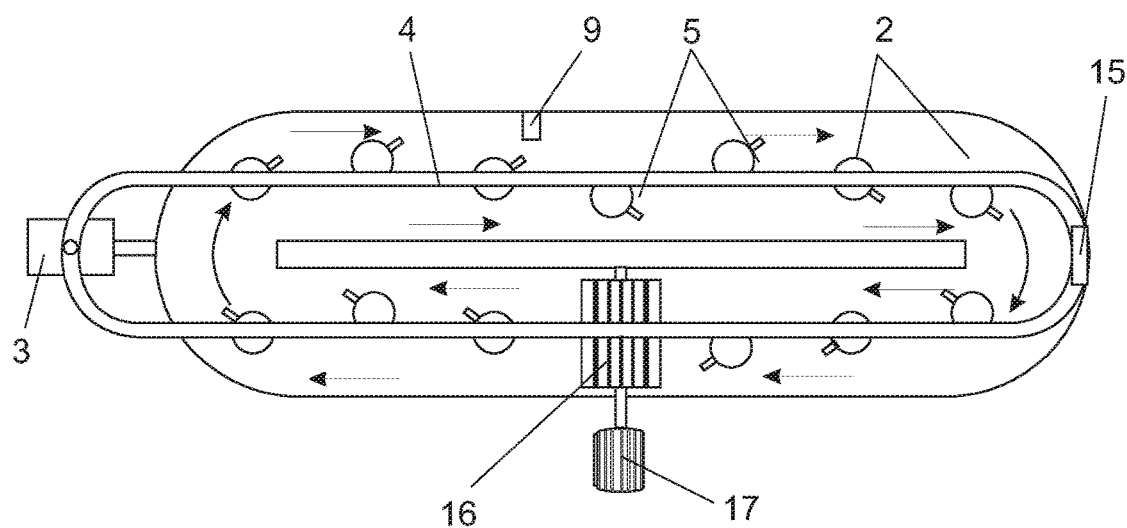
FIG. 2 is a plan view thereof.

In the embodiment of prototype microalgae cultivation equipment illustrated in FIGS. 1 and 2 of the drawings, microalgae cultivation equipment for the cultivation of microalgae includes a raceway (1) defining an endless channel for the circulation of liquid growth medium therein as shown in FIG. 2. Multiple generally upright photobioreactor columns (2) are spaced apart along the length and across the breadth of the raceway and are supported in an upright condition with their lowermost ends immersed, in use, in the liquid growth medium contained in the raceway such that growth medium may be discharged from the photobioreactor columns directly into the raceway and below the surface of liquid growth medium contained in the raceway. The photobioreactor columns can be fixed onto the bottom of the raceway; made to stand on the bottom of the raceway supported by their own weight; or they can be supported in any suitable manner such as by way of a supporting frame to which they can be attached or from which they can be suspended.

The bottom part of a vertical column photobioreactor column may be made of any suitable and durable material such as unplasticised polyvinylchloride, and may take on any suitable shape that would allow satisfactory liquid flow patterns to be developed as contemplated by this invention.

The upper part of the photobioreactor column may be made from any transparent material capable of allowing visible light through into the growth medium contained in the photobioreactor column. Examples of suitable materials include clear plasticised polyvinylchloride, polycarbonate, poly(methyl methacrylate) such as that sold under the trade name Perspex™, etc. It is preferable that the transparent material be as thin as practically possible so as to reduce the cost of construction and to allow the maximum amount of light through into the growth medium. For plasticised polyvinylchloride, wall thicknesses of 0.5 to 1 mm are preferred, while for polycarbonate, the wall thickness can vary from as low as 0.3 to 0.75 mm whilst maintaining sufficient structural integrity to support a column of water that may range from 1.0 m to 1.6 m in height and up to 0.30 m and more generally about 0.25 m in diameter.

The diameter of the photobioreactor column is preferably chosen so as to at least double the available surface area of growth medium for the capturing of photons, whilst at the same time has a total holding capacity of all of the photobioreactor columns is calculated to be between 20 and 30% of the growth medium of the total integrated cultivation system.

Smaller diameter photobioreactor columns are more efficient from the point of view of capturing photons due to the penetration of light into the growth medium, but has a significantly smaller growth medium holding capacity compared to larger diameter photobioreactor columns. It is preferable that the diameter of the photobioreactor columns closely approximates the total depth of growth medium in the raceway part of the growth system, which typically varies from 150 mm to 300 mm. For this reason, photobioreactor column diameters ranging from 100 to 300 mm, and more preferably from 120 to 250 mm are preferred.

Figure 3:
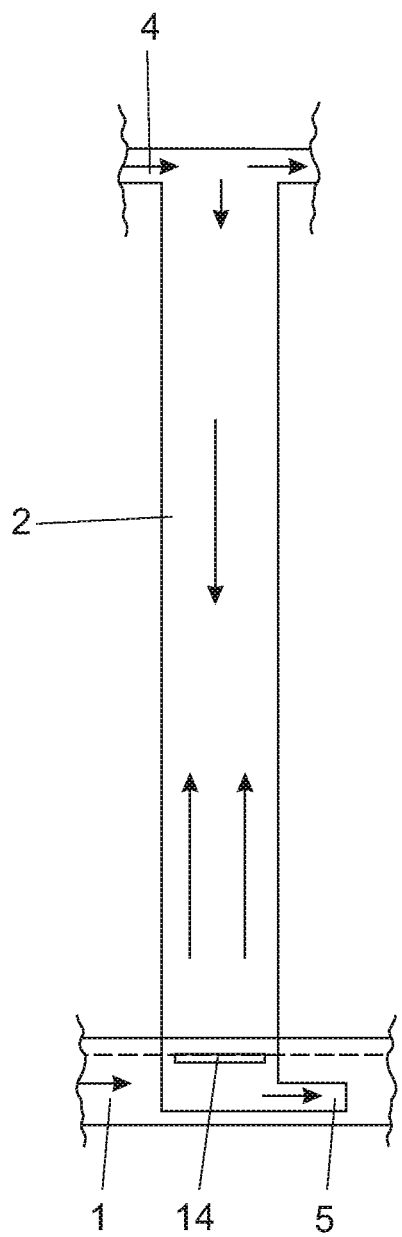
FIG. 3 illustrates schematically in elevation one flow pattern within a vertical photobioreactor column.

In the arrangement illustrated in FIGS. 1 and 3, a low shear pump (3) is provided for withdrawing liquid growth medium from the raceway and transferring it to an uppermost region of the photobioreactor columns to a manifold pipe (4) interconnecting the upper ends of the photobioreactor columns so that liquid growth medium is distributed to the upper ends of all of the photobioreactor columns. The size of the manifold pipe (4) and delivery columns to the top of each photobioreactor column can be sized so as to ensure equal, or nearly equal, flow rates to each individual photobioreactor column.

The liquid growth medium thus circulates from the raceway through the manifold pipe to the upper ends of the photobioreactor columns and flows down the photobioreactor columns to become discharged back into the raceway at the lower end thereof below the liquid surface in the raceway. A restriction in the form of a small diameter outlet pipe (5) at the bottom of each photobioreactor column controls the outflow of liquid growth medium into the raceway. By carefully balancing the rate of inflow and outflow to the photobioreactor columns, the liquid height of the growth medium in the vertical photobioreactor columns can be controlled. It is preferable that the liquid height be as high as possible to maximise the surface area of growth medium exposed to light. The small diameter outlet pipes are arranged generally horizontally but may be inclined somewhat either upwards or downwards relative to the general flow direction and/or inclined at a sideways angle to the general flow direction, at least to some extent, in order to create a desired mixing action of algae and liquid growth medium in the raceway.

A gas inlet arrangement (14) provides gas bubbles in the form of $CO_2$ enriched air that pass upwards in each of the photobioreactor columns in use in order to make available a supply of $CO_2$ for the growth of microalgae and also to provide agitation to enhance microalgae growth. The $CO_2$ enriched air is sparged into each individual photobioreactor tube and not directly into the raceway so as to control the available $CO_2$ throughout the entire growth system comprising the raceway pond and vertical photobioreactor columns by either increasing the liquid flow rate through the photobioreactor column, or by increasing the concentration of $CO_2$ in the air, or both.

In a carefully balanced growth system, $CO_2$ will be available to the growing microalgae through the chemical equilibrium:

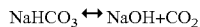

$$NaHCO_3 \leftrightarrow NaOH + CO_2$$

As the level of $CO_2$ falls, more NaOH is released and the pH of the growth medium rises. To ensure growth conditions that are not carbon-limited consequent on too little $CO_2$ being available, the equilibrium above must continuously be kept in balance so that the rate of $CO_2$ supply through sparging $CO_2$ enriched air through the vertical column photobioreactor columns is matched with the rate at which the microalgae consume $CO_2$ during photosynthesis.

This may very conveniently be achieved by monitoring the pH of the liquid growth medium using a pH monitor (9) so that the pH of the growth medium throughout the growth system is maintained between very narrow limits. For most microalgae species, the optimum pH range falls approximately in the region of 7.5 to 8.5 and in a carefully balanced growth system the pH variation should not exceed 0.5 pH units through the efficient supply and uptake of $CO_2$ as contemplated above.

For persons skilled in the art it should be obvious that during periods of low photosynthetic activity, the rate of $CO_2$ assimilation by microalgae will be low and the supply of $CO_2$ can be reduced by either reducing the concentration of $CO_2$ in the sparging air, or by reducing the rate of recirculation of the growth medium. During periods of no photosynthetic activity, recirculation may be stopped completely and the $CO_2$ concentration in the sparging air reduced terminating the supply of $CO_2$ to the sparging air.

During periods of high photosynthetic activity, the supply of $CO_2$ must be increased as contemplated above to maintain the pH levels of the growth medium within the narrow limits as specified.

In order to maintain the pH balance of an entire growth system through manipulation of $CO_2$ supply, maximum growth rates can be achieved through avoiding carbon-limited growth conditions. Achieving this particular objective requires that sufficient $CO_2$ be supplied under a wide variety of environmental conditions, and hence a wide range of growth rates. In particular, the supply of $CO_2$ should be able to meet these objectives even under the most $CO_2$ demanding conditions, i.e. when growth rates are very high. Such conditions prevail when the environmental temperature is in the optimum range for microalgae growth, there are high levels of sunlight, there are sufficient levels of macro- and micronutrients in the liquid growth medium, and the concentration of microalgae within the growth medium is high. To meet sufficient rates of $CO_2$ replacement under such conditions require it is important that sufficient vertical column elements be provided inside the growth system where $CO_2$ may be supplied. It is preferable that the number and size of such vertical columns be sufficient to hold between 5 and 30% of the total amount of growth medium contained within the entire growth system.

One or more horizontal paddle wheels (16) dip into the liquid nutrient medium in the raceway such that upon rotation by a suitable power source such as an electric motor (17), a flow of liquid growth medium within the endless channel of the raceway along its length is created. The linear flow velocity of the growth medium along the endless channel has been the subject of many studies and should be sufficient so as to minimise the settling of microalgae from the growth medium. Linear flow velocities of between 20 and 30 cm/second are generally considered sufficient.

An elevated gas separation reservoir (15) may be associated with the upper ends of the photobioreactor columns and the manifold tube for discharging oxygen enriched gasses from the photobioreactor and to act as a demister to limit water loss from the continuously sparged photobioreactor columns.

One of the main shortcomings of a traditional raceway is its poor surface area to volume ratio, which has a direct impact upon the system's ability to capture photons effectively. In a typical example of the system described according to this invention, vertical photobioreactor columns with a liquid height of 1.4 m above the surface of the liquid growth medium in the raceway that is 250 mm in depth have been added at 1 m intervals along the length of the raceway. Thus for a system with the dimensions of about a 14 metre length of raceway channel; a 1 metre width; and 13 upright photobioreactor columns, the surface area to volume ratio of the raceway without any vertical columns would be 4 (volume=3.786 m$^3$; area=15.143 m$^2$). However, with the added photobioreactor columns the ratio increases to 6.3 (volume=4.68 m$^3$; area=29.50 m$^2$). This represents an increase of approximately 95% in available surface area, thereby nearly doubling the effective surface area of the raceway system. The growth medium contained within the thirteen vertical column photobioreactor elements amounts to about 19% of the total growth medium holding capacity of the growth system.

Apart from a poor surface area to volume ratio, traditional raceways also suffer from poor gas-liquid mass transfer rates. This is mainly due to the shallow nature of such cultivation systems with the liquid depth typically varying between about 0.25 and 0.35 m. By effectively adding height to the raceway system by means of the vertical photobioreactor columns, the gas-liquid mass transfer efficiency of the system can be significantly improved by introducing the gasses into the photobioreactor columns rather than into the raceway itself.

Figure 4:
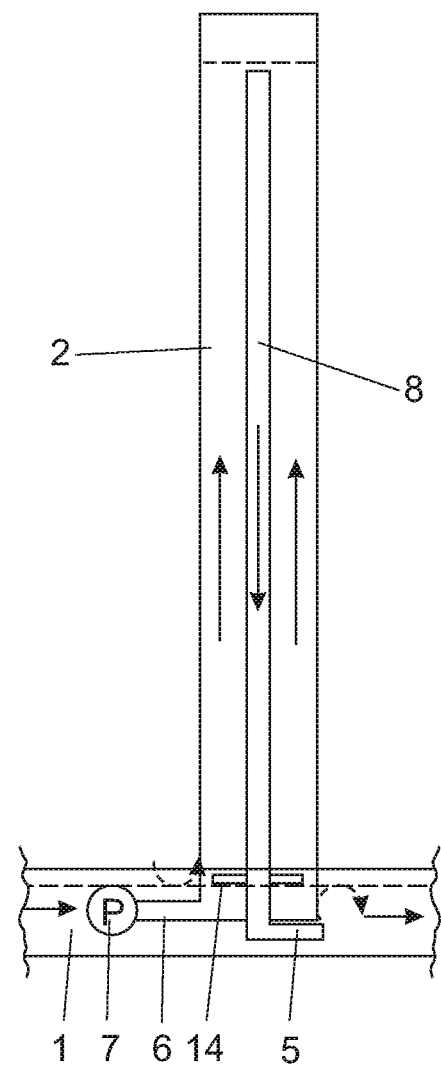
FIG. 4 illustrates schematically in elevation an alternative flow pattern within a vertical photobioreactor column.

As an alternative to the use of an elevated manifold tube to feed liquid nutrient medium to the photobioreactor column, liquid nutrient medium may be fed from the bottom of each vertical photobioreactor tube and in such an instance an overflow at the top of the vertical photobioreactor column is provided into a central gravity drainage tube (8) to control the height of the liquid in the photobioreactor column, as shown in FIG. 4.

Figure 5:
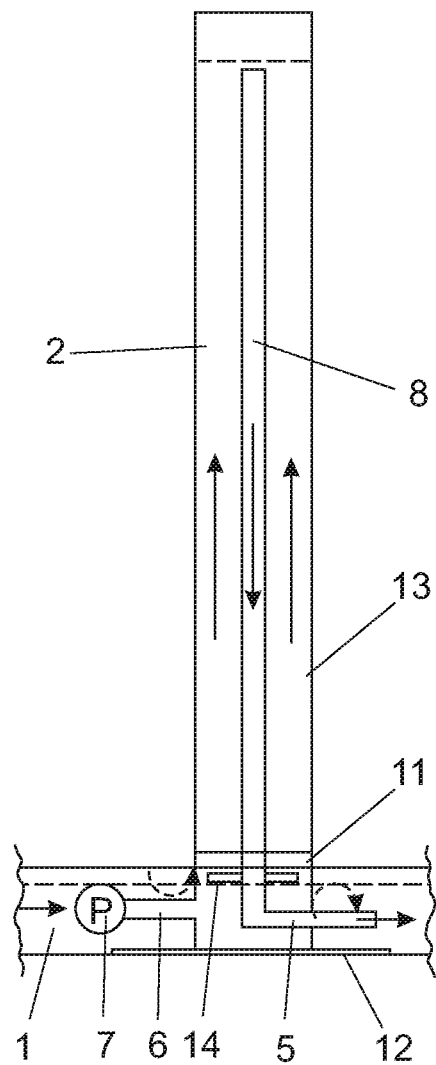
FIG. 5 illustrates schematically in elevation a free standing photobioreactor column using the alternative flow pattern illustrated in FIG. 4.
Figure 6:
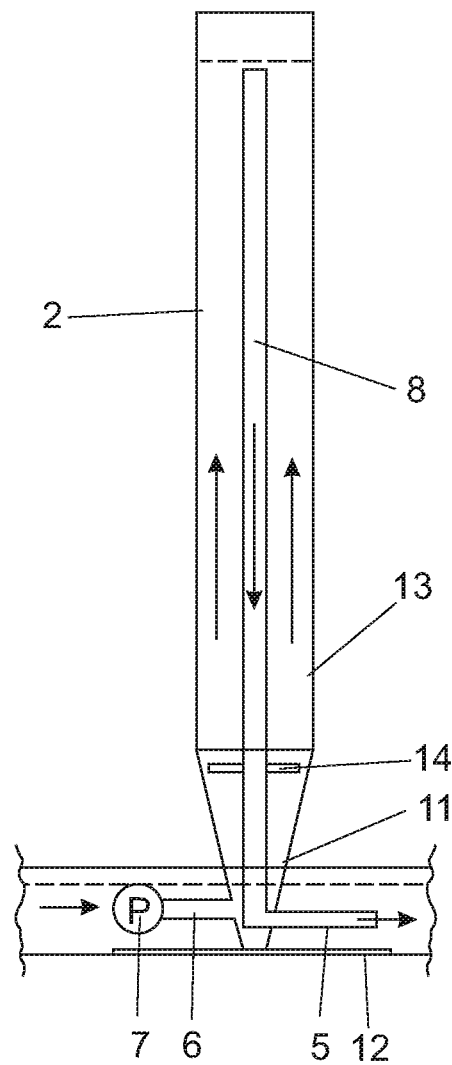
FIG. 6 illustrates schematically in elevation an alternative free standing photobioreactor column using the alternative flow pattern illustrated in FIG. 4.

The photobioreactor columns may, as illustrated in FIGS. 5 and 6, be made in two parts namely a bottom part (11) that may have a base plate (12) to render the filled photobioreactor column self-standing with an upper tubular part (13) carried by the bottom part. In such an instance, the bottom part of each vertical photobioreactor column may be made of any suitable and durable material such as rigid un-plasticized polyvinylchloride, and may take on any suitable shape that would allow liquid flow patterns as contemplated in this invention. In the arrangement illustrated in FIG. 5, the bottom of the bottom part may be fixed directly to the base plate. In the instance illustrated in FIG. 6, the bottom part may have an upwardly directed conical entrance for liquid nutrient medium supplied by the low shear pump (7).

A gas inlet arrangement (14) provides gas bubbles in the form of $CO_2$ enriched air that pass upwards in each of the photobioreactor columns in use in order to make available a supply of $CO_2$ for the growth of microalgae and also to provide agitation to enhance the growth of microalgae. The $CO_2$ enriched air is sparged into each individual photobioreactor column and not directly into the raceway so as to control the available $CO_2$ throughout the entire growth system comprising the raceway and vertical photobioreactor columns by either increasing the liquid flow rate through the photobioreactor columns, or by increasing the concentration of $CO_2$ in the air, or both.

Due to the turbulent mixing inside the vertical photobioreactor column in each instance, the difference in mass transfer efficiency between the counter-current flow and co-current flow patterns is expected to be practically negligible.

Figure 7:
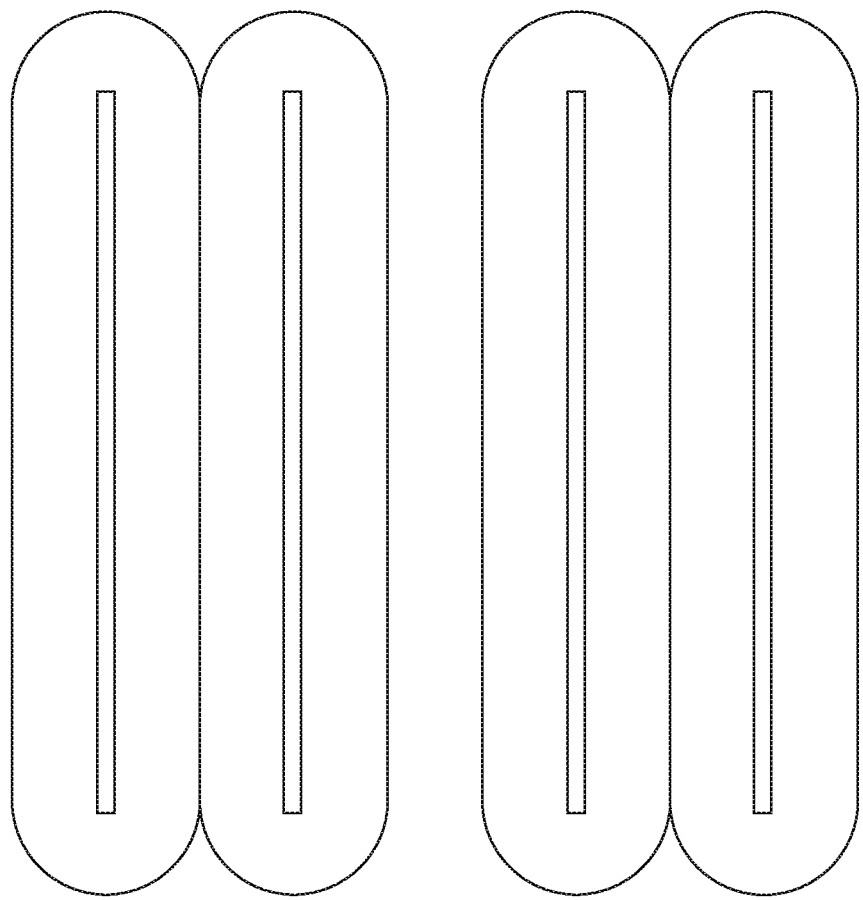
FIG. 7 is a schematic plan view of a number of raceways located within a specific geographic area.
Figure 8:
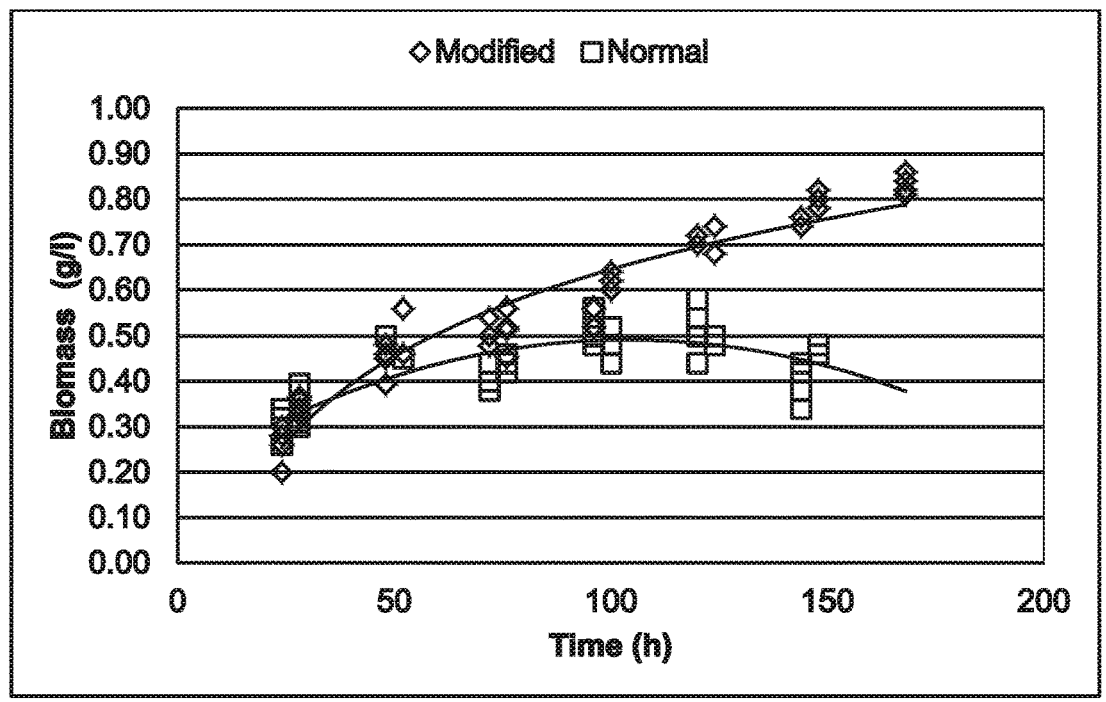
FIG. 8 is a graphic comparison between the performance of a modified raceway according to the invention and a normal raceway.
Figure 9:
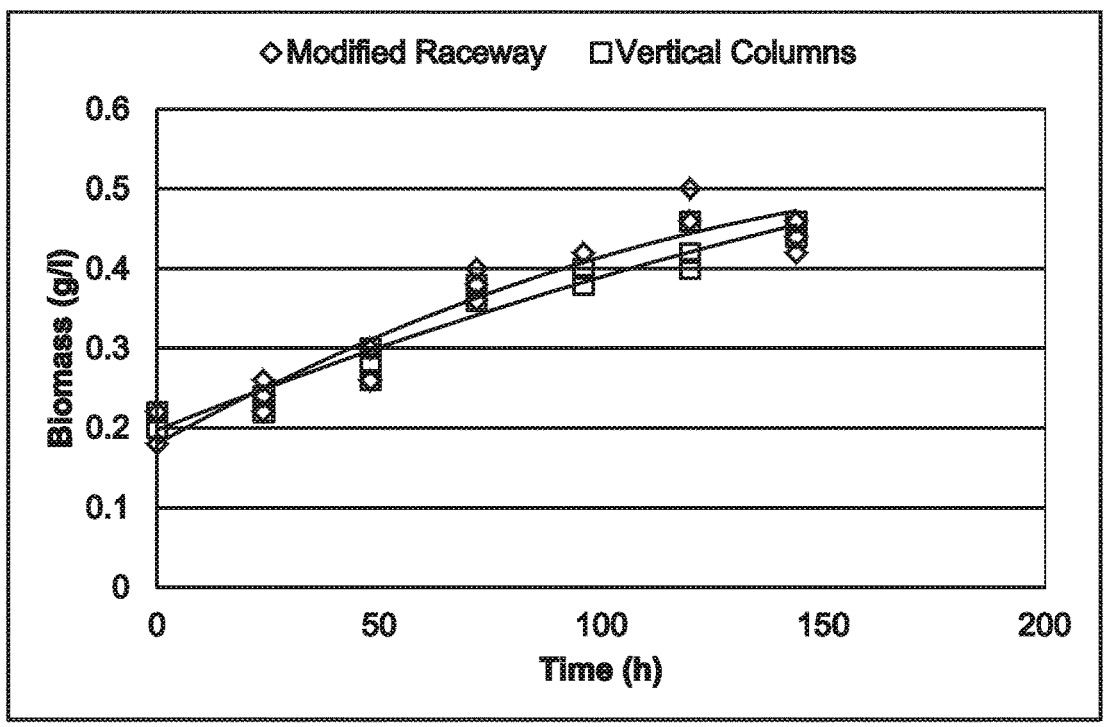
FIG. 9 is a graphic comparison between the performance of a modified raceway according to the invention and a conventional vertical-column photobioreactor assembly; and, FIG. 10 is a graphic illustrating the effectiveness of the modified raceway cultivation equipment to transfer $CO_2$ effectively from the gas-phase to the liquid phase and compares the variation of pH of normal raceway cultivation equipment with the variation in pH of modified raceway cultivation equipment.

The modified raceway design drastically reduces the number of vertical photobioreactor column required per unit area when compared to a growth system comprising only vertical photobioreactor column only. As example, for a growth system with a total growth medium capacity of approximately 2000 $m^3$, a tubular system would require approximately 27,000 vertical columns (each column holding approximately 76 L), but for a modified raceway with the same growth medium capacity of 26 single raceways with a capacity of about 80 $m^3$ per raceway, the number of columns required is reduced to only 5500. This not only represents a significant saving in capital costs, but also in operating costs. FIG. 7 illustrates one arrangement of multiple oval raceways that can be arranged on an area of land.

In testing the system described above, air enriched with $CO_2$ was sparged at a rate of 1.5 L of air per kilogram growth medium/h in the vertical photobioreactor column of a tubular photobioreactor system, and at the same rate in the vertical photobioreactor column of the modified raceway. Since the volume of air required for the modified raceway cultivation system is determined by the growth medium volume contained only in the vertical photobioreactor column and not the entire volume of the growth system, the comparative volume reduction in air mixture required is approximately 80%, which represents a substantial energy saving. Although the modified raceway does require pumping of the growth medium through the vertical photobioreactor column, pumping water is significantly more energy efficient than blowing air, and pumping is only required during active photosynthetic periods while air requires sparging 24 hours per day for agitation purposes. The comparison of growth performance for these tow cultivation systems (tubular versus modified raceway) is illustrated graphically over a 140 hour test period in FIG. 7 from which it is noted that the comparison is very favourable bearing in mind the savings in capital and running costs.

A further feature of the modified raceway as compared to a traditional raceway is the change in liquid flow pattern around the raceway. In a traditional raceway, vertical mixing of the growth medium is quite restricted, especially for large raceways with long distances between paddlewheel mixers. In the modified raceway, however, the vertical columns placed in the centre of the flow stream results in areas of high and low liquid pressure before and after the column. This results in an upward movement of the liquid on the high pressure side of the column, while a downward movement is obtained on the opposite side as indicated in FIG. 4.

Furthermore, by directing the outflows at the bottom of the columns as shown in FIGS. 2 and 3, both vertical flow and lateral flow along the sides of the raceway may be improved. This improvement in vertical mixing in the channel part of the modified raceway cultivation system not only improves the photon capturing capability of the channel part of the cultivation system by moving microalgae cells to and from the surface of the growth medium, but also significantly improves the carrying capacity (defined as the maximum amount of biomass that can be supported in the growth medium before biomass starts settling out of the growth medium) compared to a traditional raceway cultivation system as shown by the comparative results in Table 1. High carrying capacities are highly desirable since the higher the carrying capacity the higher is the productivity of the system.

The modified raceway system of the invention is easy to construct, operate and maintain. Its basic operation is essentially the same as practiced for normal raceway systems and may be operated in batch, semi-batch, or continuous modes. A comparison between the biomass accumulation for a traditional raceway cultivation system and the modified raceway system is illustrated graphically over a 180 hour test period in FIG. 6 from which it is noted that the comparison is very favourable bearing in mind the improved conditions.

TABLE 1

Comparitive growth performance measures for three cultivation systems

| | Modified Raceway | Normal Raceway | Vertical Column PBR |
|---|---|---|---|
| Specific growth rate ($d^{-1}$) | 0.2511 | 0.1269 | — |
| | 0.2189 | — | 0.1674 |
| Biomass accumulation rate ($h^{-1}$) | 0.0243 | 0.0068 | — |
| | 0.0201* | — | 0.0156* |
| Carrying capacity (g/L) | 1.0163 | 0.5354 | — |
| | 0.5226* | — | 0.5354* |

*This comparison suffered 4 hours/day power outages for four of the experimental days Numerous variations may be made to what is described above without departing from the scope of this invention, as will be quite apparent to those skilled in the art.

Figure 10:
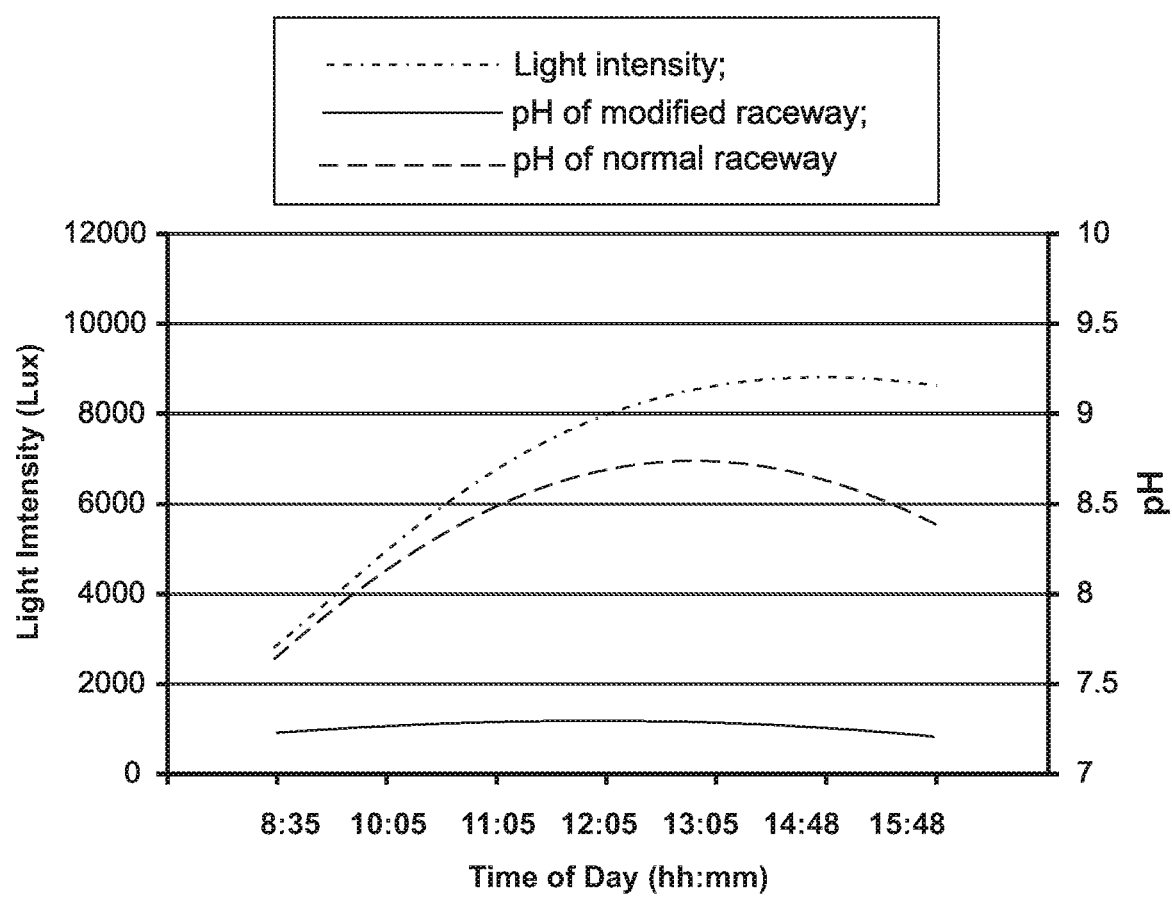

FIG. 10 illustrates the effectiveness of the modified raceway cultivation equipment to transfer $CO_2$ effectively from the gas-phase to the liquid phase in an actively growing microalgae culture. FIG. 10 compares the variation of pH of normal raceway cultivation equipment with the variation in pH of a modified raceway cultivation equipment over a period of one day by taking regular pH and light intensity measurements. Both assemblies of cultivation equipment were sparged with the same $CO_2$—air mixture, the only difference being that the mixture was sparged directly to the bottom of the raceway for the normal raceway, but for the modified raceway, the mixture was sparged only to the bottom of each vertical photobioreactor column. The results clearly show that as the light intensity increases during the day, the pH of the normal raceway increases whilst the pH of the modified raceway is kept essentially constant.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. Microalgae cultivation equipment for the cultivation of microalgae, the cultivation equipment comprising:
   a raceway component with a raceway defining an endless channel for the circulation of liquid growth medium therein;
   a flow inducing arrangement for inducing a flow of liquid growth medium within the endless channel of the raceway, the flow inducing arrangement comprising at least one of a paddle wheel or a jet pump;
   an integrated second component comprising multiple vertical photobioreactor columns, i) configured to contain, in use, between 5 and 30% of the total volume of liquid growth medium in the microalgae cultivation equipment, ii) spaced apart along the length of the raceway and across the breadth of the raceway inside the raceway so that the photobioreactor columns are in the centre of the flow stream of liquid growth medium, and iii) supported in an upright condition such that their lowermost ends discharge liquid growth medium in use into liquid growth medium in the raceway;
   a circulation promoting facility comprising a low shear pump for causing liquid growth medium to circulate from the raceway component through the photobioreactor columns to become discharged back into the raceway; and
   one or more gas inlets for providing gas bubbles, in use, passing upwards in each of the photobioreactor columns,
   wherein the photobioreactor columns each comprise an overflow tube inside each of the photobioreactor columns configured to receive and direct an overflown liquid growth medium back into the raceway; and have one or more small diameter outlet pipes arranged generally horizontally below the liquid surface level of the raceway component to return the overflown liquid growth medium from the vertical photobioreactor columns to the raceway.

2. Microalgae cultivation equipment according to claim 1 in which the equipment is configured such that in use an exposed surface area of growth medium to direct light or sunlight in the photobioreactor columns is between 50 and 200% that of an exposed surface area of growth medium in the raceway alone without the photobioreactor columns.

3. Microalgae cultivation equipment according to claim 2 in which the exposed surface area of growth medium to direct light or sunlight is between 50 and 120% that of an exposed surface area of growth medium in the raceway alone without the photobioreactor columns.

4. Microalgae cultivation equipment according to claim 1 in which the photobioreactor columns have a diameter of from 100 mm to 300 mm and a height of from 1.0 to 1.6 m.

5. Microalgae cultivation equipment according to claim 1 in which the low shear pump is configured to:
   withdraw liquid growth medium from the raceway; and
   transfer the withdrawn liquid growth medium to a manifold pipe interconnecting the upper ends of the photobioreactor columns so as to distribute liquid growth medium to the upper ends of multiple photobioreactor columns.

6. Microalgae cultivation equipment according to claim 1 in which the low-shear pump is configured to:
   withdraw liquid growth medium from the raceway of the cultivation equipment; and
   pump the withdrawn liquid growth medium into the photobioreactor columns from the bottom and cause the withdrawn liquid growth medium to flow upwards and overflow.

7. Microalgae cultivation equipment according to claim 1 in which an elevated gas separation reservoir is associated with the upper ends of the photobioreactor columns for discharging oxygen enriched gasses from the photobioreactor columns and to act as a de-misting zone to limit loss of liquid growth medium from the photobioreactor columns.

8. Microalgae cultivation equipment according to claim 1 in which an inlet is provided for $CO_2$ enriched air to be sparged into each individual photobioreactor column so as to control the availability of $CO_2$ by either increasing or decreasing the liquid flow rate through the photobioreactor columns, or by increasing or decreasing the concentration of $CO_2$ in the air, or both.

9. Microalgae cultivation equipment according to claim 8 in which the inlets for gas to the photobioreactor columns are the only gas inlets to the equipment with no additional gas inlets being provided to the raceway itself.

10. Microalgae cultivation equipment according to claim 1 in which sufficient air is admixed with $CO_2$ present in gasses introduced into the liquid growth medium to cause turbulence inside the photobioreactor columns.

11. Microalgae cultivation equipment according to claim 1 in which a pH monitor is provided for monitoring the pH of the liquid growth medium in order to control the availability of $CO_2$ contained inside the growth medium by varying the $CO_2$ content of air used to sparge the photobioreactor columns.

12. Microalgae cultivation equipment according to claim 1 in which the outlet pipes are inclined either upwards or downwards or inclined sideways in order to create a mixing action of algae and liquid growth medium in the raceway in use.

* * * * *